(12) United States Patent
Sauer et al.

(10) Patent No.: US 7,774,044 B2
(45) Date of Patent: Aug. 10, 2010

(54) SYSTEM AND METHOD FOR AUGMENTED REALITY NAVIGATION IN A MEDICAL INTERVENTION PROCEDURE

(75) Inventors: Frank Sauer, Princeton, NJ (US); Ali Khamene, Princeton, NJ (US); Sebastian Vogt, Princeton, NJ (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1433 days.

(21) Appl. No.: 11/056,317

(22) Filed: Feb. 11, 2005

(65) Prior Publication Data

US 2005/0203380 A1    Sep. 15, 2005

Related U.S. Application Data

(60) Provisional application No. 60/545,115, filed on Feb. 17, 2004.

(51) Int. Cl.
*A61B 5/05* (2006.01)
*G09G 5/00* (2006.01)

(52) U.S. Cl. ............... 600/424; 600/411; 345/8

(58) Field of Classification Search ............ 600/426, 600/427, 429, 439, 417, 424, 411; 354/126; 359/850, 462, 630, 51; 345/8–9; 382/128, 382/130–133
See application file for complete search history.

(56) References Cited

U.S. PATENT DOCUMENTS

| | | | | |
|---|---|---|---|---|
| 5,464,410 A | * | 11/1995 | Skeens et al. | 606/130 |
| 5,912,776 A | * | 6/1999 | Yaginuma | 359/850 |
| 6,122,541 A | * | 9/2000 | Cosman et al. | 600/426 |
| 6,129,670 A | * | 10/2000 | Burdette et al. | 600/427 |
| 6,146,380 A | * | 11/2000 | Racz et al. | 606/41 |
| 6,246,900 B1 | * | 6/2001 | Cosman et al. | 600/426 |
| 2002/0075201 A1 | * | 6/2002 | Sauer et al. | 345/7 |
| 2004/0267121 A1 | * | 12/2004 | Sarvazyan et al. | 600/439 |
| 2007/0032906 A1 | * | 2/2007 | Sutherland et al. | 700/248 |

OTHER PUBLICATIONS

State et al (Superior augmented Reality Registration by Integrating Landmark Tracking and Magnetic Tracking (www.cs.unc.edu/~us/hybrid.html)).*

* cited by examiner

*Primary Examiner*—Eric F Winakur
*Assistant Examiner*—Lawrence N Laryea
(74) *Attorney, Agent, or Firm*—Donald B. Paschburg; F.Chau & Associates, LLC (57) ABSTRACT

A method for augmented reality navigation of a medical intervention includes providing a stereoscopic head mounted display, the display including a pair of stereo viewing cameras, at least one tracking camera, and a stereoscopic guidance display. During a medical intervention on a patient, the patient's body pose is determined from a rigid body transformation between the tracking camera and frame markers on the scanning table, and the pose of an intervention instrument with respect to the table is determined. A visual representation of the patient overlaid with an image of the intervention target, the instrument, and a path for guiding the instrument to perform said medical intervention is displayed in the stereoscopic guidance display.

22 Claims, 5 Drawing Sheets

SYSTEM AND METHOD FOR AUGMENTED REALITY NAVIGATION IN A MEDICAL INTERVENTION PROCEDURE

CROSS REFERENCE TO RELATED UNITED STATES APPLICATIONS

This application claims priority from "An Augmented Reality System and Setup for MR Guided Interventional Procedures", U.S. Provisional Application No. 60/545,115 of Frank Sauer, et al., filed Feb. 17, 2004, the contents of which are incorporated herein by reference.

TECHNICAL FIELD

The invention is directed to augmented reality navigation systems in medical diagnostic imaging.

DISCUSSION OF THE RELATED ART

Magnetic resonance (MR) imaging information can be utilized to guide minimally invasive medical intervention procedures. MR scanners with closed magnets are now widely available and deliver a higher image quality than scanners with open magnets. When using a scanner with closed magnets, the procedure is usually performed in an iterative way. The patient is moved out of the scanner to advance the interventional instrument and moved into the scanner to acquire new images. This "stop-and-go" method ensures stepwise monitoring of the procedure, but requires many interruptions of the actual intervention. An augmented reality (AR) image guidance system can map medical imaging information onto a patient's body. Anatomical structures can be visually displayed at the location where they actually are, a concept referred to as in-situ visualization. With this visual display, a physician can observe directly a patient's internal anatomy. The patient's body appears transparent. In-situ visualization is a direct way of presenting medical imaging information, and has the potential to guide minimally invasive procedures very intuitively. AR visualization has found an increasing number of applications in the medical field. At the University of North Carolina, AR has been investigated for use with ultrasound-guided procedures and for laparoscopic surgery. At Harvard/MIT, a system for interventional MRI has been developed where the surgeon is provided with an augmented video image taken with a single video camera and displayed on a monitor above the patient. At Guy's and St Thomas' Hospitals in London, a stereo augmented reality system has been implemented on a surgical microscope. At the AKH in Vienna, a head-mounted operating microscope has been equipped for AR visualization.

SUMMARY OF THE INVENTION

Exemplary embodiments of the invention as described herein generally include augmented reality systems and methods for performing guided medical intervention procedures.

In an aspect of the invention, there is provided a system for augmented reality navigation during a medical intervention, including a stereoscopic head mounted display including a pair of stereo viewing cameras, at least one tracking camera, and a stereoscopic guidance monitor, a plurality of markers on a frame attached to a table, a medical instrument for performing said medical intervention, said instrument including a plurality of markers, and a control component, said control component accepting signals from said viewing cameras and tracking camera to generate an image for display in said stereoscopic guidance monitor. The control component includes a program storage device readable by a computer, tangibly embodying a program of instructions executable by the computer to perform the method steps for determining a rigid body transformation between the tracking camera and the frame markers, determining a patient's body pose from said rigid body transformation, during a medical intervention on said patient, wherein said patient is positioned on said table, determining the pose of said medical instrument with respect to the table from the patient's body pose and said instrument markers, and displaying in the guidance display a visual representation of said patient, said instrument, and a path for guiding said instrument to perform said medical intervention. The visual representation of said patient is overlaid with an image of a target of said intervention.

In another aspect of the invention, the tracking camera is sensitive to the near-infrared spectrum, and comprises a wide angle lens and a ring shaped infrared flash.

In another aspect of the invention, the method further comprises the step of, prior to the medical intervention, determining a rigid body transformation between the tracking camera and the viewing cameras.

In another aspect of the invention, the method further comprises the step of color-coding the visual representation of the instrument to indicate penetration of said instrument toward said target, and displaying concentric circles in the guidance display to indicate distance of the instrument to the target.

In another aspect of the invention, the method further comprises the step of, prior to the medical intervention, determining a relationship between the medical image and the tracking camera.

In another aspect of the invention, the system includes a calibration phantom including magnetic and optical markers. The calibration phantom is used to determine the relationship between the medical image and the tracking camera.

In another aspect of the invention, the method further comprises monitoring the patient's respiration during said intervention, and altering said visual representation of said patient in accordance with said respiration.

In another aspect of the invention, the image of the target is a magnetic resonance image.

In another aspect of the invention, the instrument is a biopsy needle.

In another aspect of the invention, the system further includes a plurality of tracking cameras for positioning the head mounted display.

DETAILED DESCRIPTION OF THE PREFERRED EMBODIMENTS

Exemplary embodiments of the invention as described herein generally include systems and methods for augmented reality navigation systems and setup for MR-guided interventions. In the interest of clarity, not all features of an actual implementation which are well known to those of skill in the art are described in detail herein.

In accordance with an embodiment of the invention, there is provided an AR system that is based on a stereoscopic head-mounted display (HMD) of the video-see-through variety. A stereo pair of video cameras serves as artificial eyes. A live stereoscopic video view of a real scene can be overlaid with computer graphics in real-time. Another, single head-mounted camera, which is rigidly attached to the stereo viewing cameras, is used for tracking. In one embodiment of the invention, the system uses video-see-through AR, where the combination of real and graphic views takes place in the computer. Registration can be performed in an objective way. A head-mounted display provides a stereoscopic video-view of the patient in real-time, which is augmented with three-dimensional medical information to perform procedures guided by MR and other modalities of diagnostic images. For expository purposes, the embodiments of the present invention will be explained using MR imaging as an example, however, the systems of the invention are equally applicable to other forms of imaging, including, without limitation, CT, US, PET, etc.

An exemplary, non-limiting example of an MR-guided procedure is that of needle placement. In addition to the MR image information, the scene can be augmented with 3D graphics representing a forward extension of the needle and of the needle itself. During insertion, the needle can be observed virtually at its actual location in real-time, supporting the interventional procedure in an efficient and intuitive way. The system includes sets of markers attached to the MR couch and an interventional tool, such as one or more needles. In addition, a hybrid set of markers that include optical and magnetic markers can be used for calibration. This hybrid set is incorporated into a calibration object, referred to as a calibration phantom, so that the optical markers and the magnetic markers are in known relation to each other. The calibration relates the coordinates of the optical markers to the MR image space. Systems according to the embodiments of the invention can be integrated into a MR scanner, providing a workflow for an MR guided interventional procedure.

Figure 1:
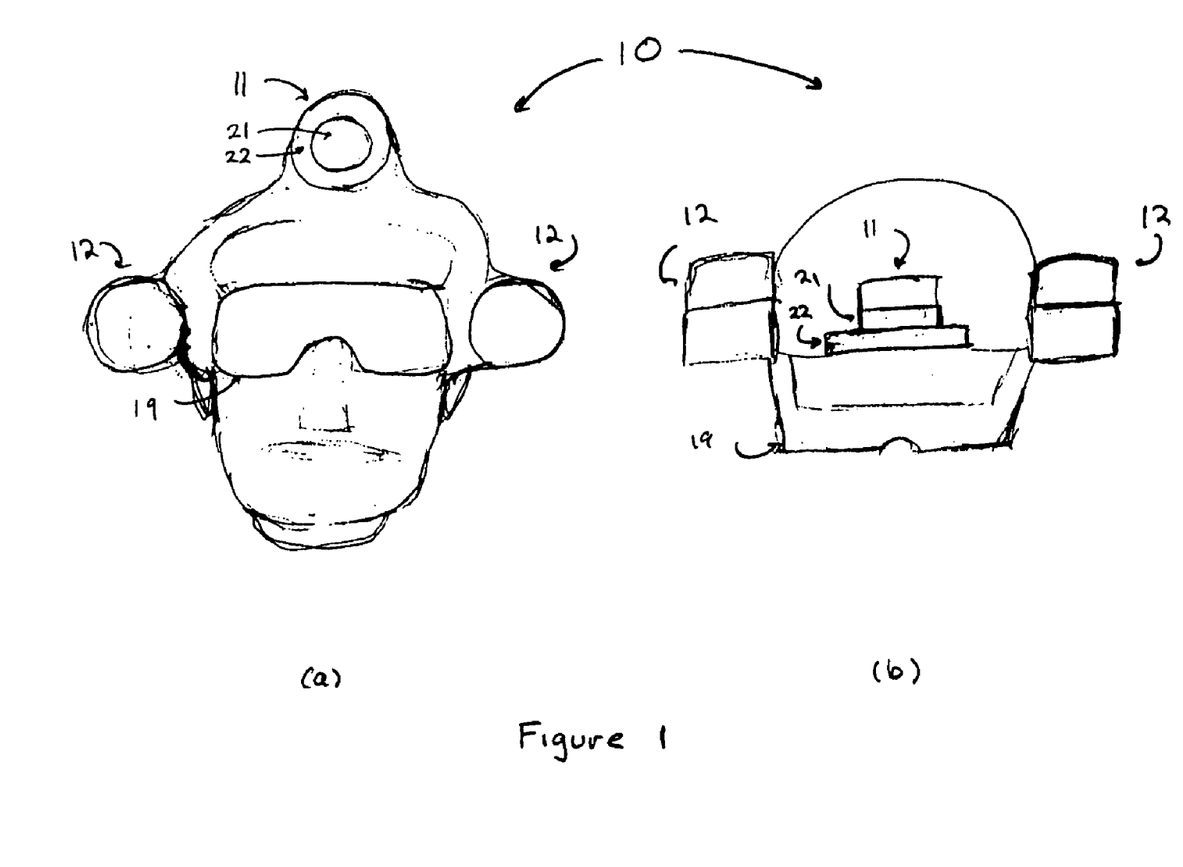
FIGS. 1a-b depict front and top views of a stereo head mounted display with tracking and scene cameras, according to an embodiment of the invention.

FIGS. 1a-b depict front and top views, respectively, of a stereo head mounted display with tracking and scene cameras, according to an embodiment of the invention, including a stereo head mounted display (HMD) 10 with tracking 11 and scene cameras 12. The camera triplet (i.e. a stereo scene camera 12 and tracking camera 11) is rigidly mounted on top of the HMD 10. Both scene cameras have fixed focus lenses and provide sharp images in about arm's length distance. The monochrome tracking camera 11, which is only sensitive in the near-infrared spectrum, is equipped with a wide-angle lens 21 and a ring shaped infrared flash 22. The user, who is wearing the HMD 10, sees in guidance display viewer 19 a stereo view of a patient overlaid with diagnostic information as provided by an MRI or other imaging modality, and with guiding graphics. Methods of guiding and positioning instruments for medical procedures are disclosed in, for example, "Augmented reality guided instrument positioning with guiding graphics", U.S. patent application Ser. No. 09/818,122, the contents of which are incorporated herein by reference in its entirety, and "Augmented and virtual reality guided instrument positioning using along-the-line-of-sight alignment", U.S. patent application Ser. No. 09/818,427, the contents of which are incorporated herein by reference in its entirety.

Figure 2:
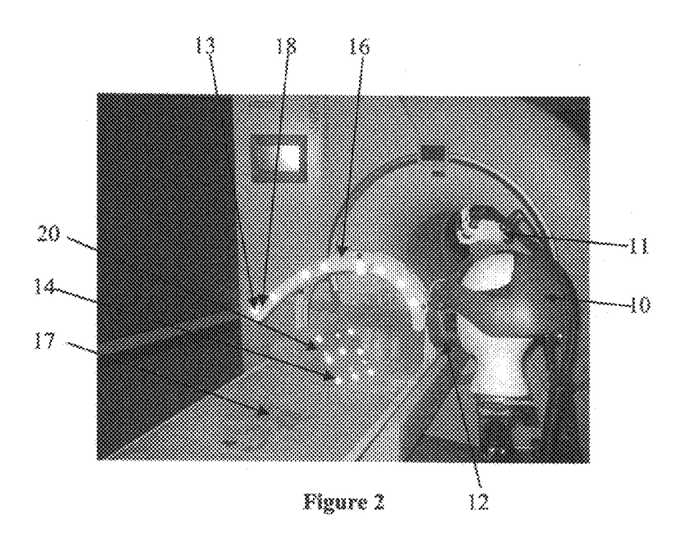
FIG. 2 depicts a stereo head mounted display and the marker set in an interventional setup, according to an embodiment of the invention.

FIG. 2 depicts a video-see-through augmented reality system setup according to an embodiment of the invention, including a stereo head mounted display (HMD) 10 with tracking 11 and scene cameras 12 and a marker set 13 surrounding an interventional workspace and a calibration phantom 20. The monochrome tracking camera 11 works in conjunction with retro-reflective optical markers 13 that are placed around the intervention workspace. The flash 22 can be synchronized with the tracker camera and permits the use of a high speed electronic shutter. This can suppress background light from incandescent and halogen lamps, which would otherwise light up the rest of the scene in the infrared spectrum, and can prevent motion blur of the retro-reflective markers resulting from fast movements of the HMD.

With a head-mounted tracker camera, the user cannot accidentally step in the way of the tracking system, making the typical line-of-sight restriction of optical tracking systems less limiting. Placing a forward looking tracker camera on the head also aids in the perceived accuracy of the augmentation, as the sensitivity of the tracking camera to registration errors can be matched to a user's sensitivity for perceiving these errors.

In order to have pose information available for each video frame (with 30 Hz frame rate), the tracker and scene cameras are genlocked. The time lag between video and graphics in the augmented video view can be eliminated, which results in a believable AR experience. During the realtime operation phase of an AR system, poses of both scene cameras (for each video frame) with respect to a patient centered coordinate system need to be estimated to overlay the 3D medical imaging data onto the patient. Referring to FIG. 2, a bridge 16 with retro-reflective markers 14 can be attached to the MR scanner table 17, thereby establishing a reference for the patient coordinate system. In an offline calibration step, the rigid body transformations between the tracker camera and the scene cameras can be determined. During the interventional procedure the rigid body transformation between the marker frame 16 and the tracker camera can be estimated. Thus, the poses of both scene cameras for each video frame with respect to the marker frame can be deduced, a procedure referred to as head tracking.

To visualize a hand-held surgical instrument, such as a biopsy needle, inside the patient's body in the AR video view, the patients body pose needs to be tracked. A cluster of retro-reflective markers 14 can be attached to the biopsy needle from which the rigid body transformation between this cluster 14 and the tracker camera for each video frame can be estimated. The pose of this hand-held instrument with respect to the scanner table can then easily be deduced from the estimated head pose from the same video frame, a procedure referred to as instrument tracking.

As shown in FIG. 2, the marker set 15 according to an embodiment of the invention can be attached to the MR scanner table and includes a bridge 16 which is double oblique cut of the surface of cylinder with the radius equal to that of MR bore. The markers 15 have a 3D distribution implemented using small posts 18 attached to the main bridge. The design provides a clear line sight for the tracking camera, while maximizing the workspace volume. Furthermore, the marker set is clear to go inside the MR bore, while the patient is on the scanner table for the scan.

According to an embodiment of the invention, the tracked instrument, such as the biopsy needle, includes a marker attachment containing set of retro-reflective markers. The size and shape of the markers are designed so that they are differentiable from the scanner table marker set within the tracking camera images.

According to an embodiment of the invention, the guidance display is the augmented reality display, where the images of the scene (i.e., patient and/or interventional site) are augmented with the information extracted with the medical images.

According to an embodiment of the invention, the interaction of the graphical representation of the tool and the target lesion can be represented using color-coding of missing and hitting of the target by the tool extension and/or direction. The in-plane distance of the tools' extension to the target can be enhanced by marking the intersection of the tool's extension with the target plane. Out of plane distance can be shown using concentric rings, where the radius of the ring depicts the distance of the tool's tip and the target parallel to the target's plane normal.

Figure 3:
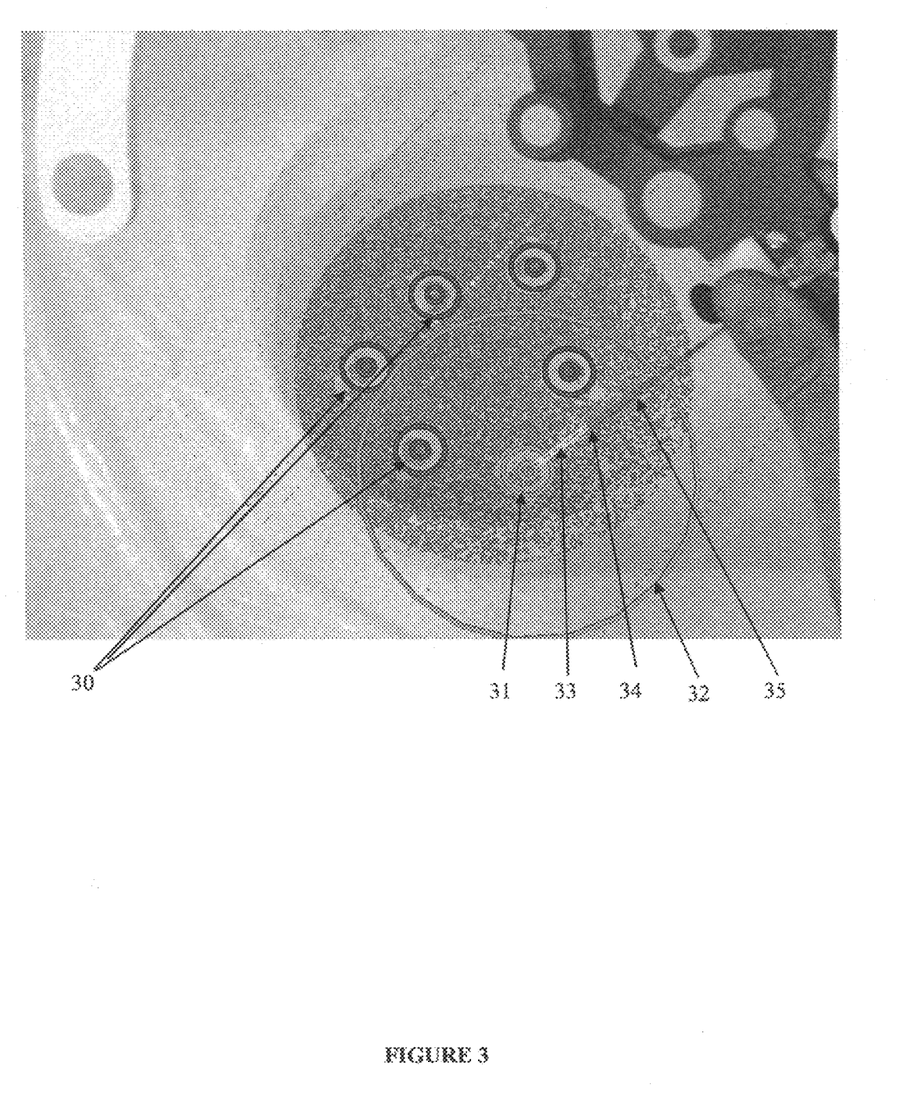
FIG. 3 depicts a monoscopic augmented view of a needle insertion guide as seen by a user, according to an embodiment of the invention.

FIG. 3 depicts a monoscopic augmented view of a needle insertion guide, according to an embodiment of the invention. In this picture, a needle is being inserted into a gel phantom that contains a set of six targets 30. A slice of an MR image is overlaid onto the video view, while both the location of six targets and the extended path of the needle are modeled and overlaid graphically onto the video image. The user would actually see a stereo image in the head-mounted display for good spatial perception. Target 31 is the currently selected target. The shaded cylinder 35 indicates the inserted portion of the actual needle, the sphere 34 indicates the location of the actual needle tip, and the cylinder 33 is an extrapolation of the needle along a straight path, allowing the user to aim precisely at the target from a distance, before and during insertion of the needle. The large concentric ring 32 around the intersection of the extended needle path 33 with the target plane indicates the distance between needle tip 34 and the target plane, enhancing the user's ability to judge the depth correctly.

According to an embodiment of the invention, a calibration procedure includes a one time scanning of a calibration phantom, which can include both magnetic and optical markers. The magnetic markers segment the MR images and provide the necessary information to match up the MR coordinate frame with that of optical system established by the marker set attached to the MR couch. The calibration results will then be valid as long as the marker set is not removed from the MR couch, or if the marker set is removed, it is reproducibly repositioned.

According to an embodiment of the invention, a respiratory monitoring device is a pneumatic belt, which can be used to classify images into various stages according to the signal coming from the belt. The displayed images in the guidance system can be altered according to the stage of breathing indicated by the pneumatic belt system.

Figure 5:
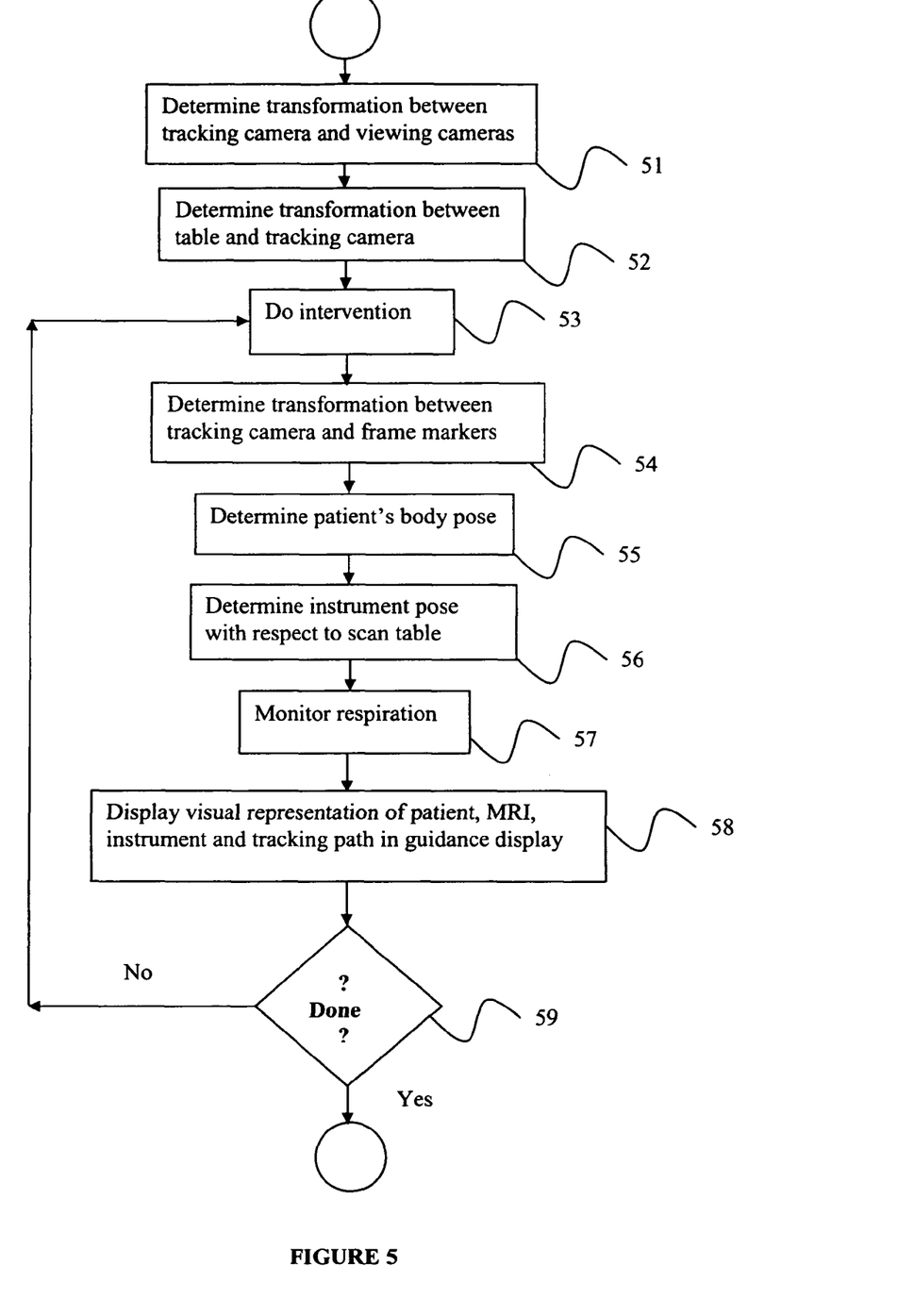
FIG. 5 presents a flow chart of an interventional procedure according to one embodiment of the invention.

FIG. 5 presents a flow chart of an MR guided interventional procedure according to one embodiment of the invention. Having provided an AR navigation system comprising the HMD according to an embodiment of the invention, a rigid body transformation between the tracking camera and the viewing cameras is determined at step 51. In addition, a rigid body transformation between the tracking camera and the scanning table, upon which a patient can be positioned, is determined at step 52. This transformation can be determined by scanning the calibration phantom, which can be equipped with magnetic and optical markers so that a relationship between a magnetic image space and an optical space can be determined. With a patient positioned on the scanning table, the intervention procedure is started at step 53. During the intervention, the rigid body transformation between tracking camera and the scanning table is determined at step 54 from optical markers attached to the frame that is part of the table. The relationship between the tracking camera and table can then be used to determine the patient's body pose at step 55. In addition, at step 56, the pose of the instrument being used for the intervention procedure is determined with respect to the scanning table from optical markers attached to the instrument, and, at step 57, the respiration of the patient is monitored. This information regarding the patient's body pose, the instrument's pose, and patient's respiration is used, along with an MRI or other modality image to generate a visual representation of the patient, the intervention target, the instrument, and tracking path to guide the instrument in the stereoscopic guidance display of the HMD at step 58. If, at step 59, the intervention procedure is still in progress, the method continues the intervention from step 53, otherwise it terminates. Note that the use of an MRI to guide the intervention procedure is exemplary and non-limiting, and images created by other modalities, such as CT scans, PET scans, or US, are within the scope of the invention.

The composite stereoscopic images (i.e., video plus the graphics from the image data) according to an embodiment of the invention provide an intuitive guidance to the interventional radiologist and/or surgeon to perform the procedure more accurately, with more confidence, and in less time. In addition, video-see-through AR allows greater control over the augmented video stream. An HMD gives the user the freedom to move around in a natural way and to inspect the scene from a variety of viewpoints. A stereoscopic HMD provides good spatial perception based on stereovision, further enhanced by kinetic depth cues.

According to another embodiment of the invention, a multi-camera system providing positioning information for the head mounted display and the interventional tools can be used as an alternative to a single tracking camera.

It is to be understood that the embodiments of the present invention can be implemented in various forms of hardware, software, firmware, special purpose processes, or a combination thereof. In one embodiment, the present invention can be implemented in software as an application program tangible embodied on a computer readable program storage device. The application program can be uploaded to, and executed by, a machine comprising any suitable architecture.

Figure 4:
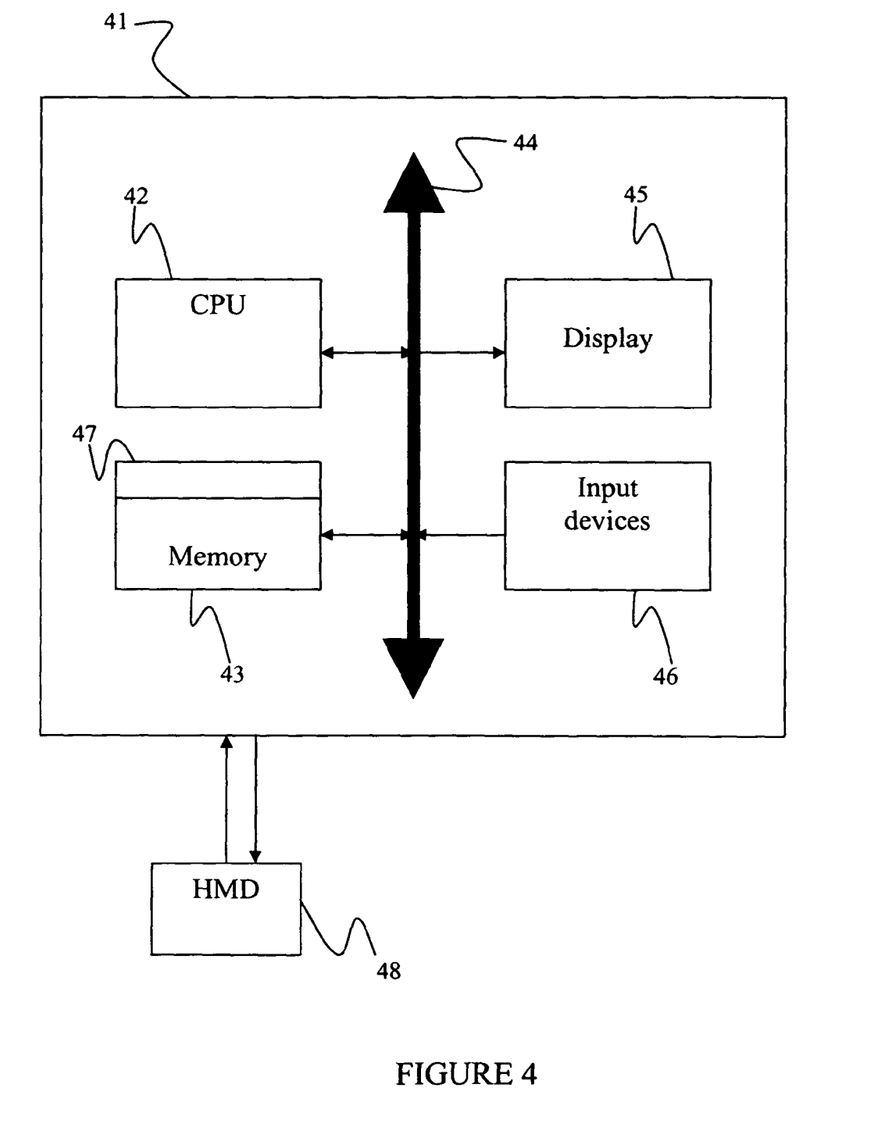
FIG. 4 depicts an exemplary computer system for implementing a preferred embodiment of the invention.

Referring now to FIG. 4, according to an embodiment of the present invention, a computer system 41 for implementing the present invention can comprise, inter alia, a central processing unit (CPU) 42, a memory 43 and an input/output (I/O) interface 44. The computer system 41 is generally coupled through the I/O interface 44 to a display 45 and various input devices 46 such as a mouse and a keyboard. The support circuits can include circuits such as cache, power supplies, clock circuits, and a communication bus. The memory 43 can include random access memory (RAM), read only memory (ROM), disk drive, tape drive, etc., or a combinations thereof. The present invention can be implemented as a routine 47 that is stored in memory 43 and executed by the CPU 42 to process the signal from the head mounted display 48, which includes the guidance display and the stereoscopic viewing cameras and tracking camera. As such, the computer system 41 is a general purpose computer system that becomes a specific purpose computer system when executing the routine 707 of the present invention. The computer system 41 also includes an operating system and micro instruction code. The various processes and functions described herein can either be part of the micro instruction code or part of the application program (or combination thereof) which is executed via the operating system. In addition, various other peripheral devices can be connected to the computer platform such as an additional data storage device and a printing device.

It is to be further understood that since the exemplary systems and methods described herein can be implemented in software, the actual method steps may differ depending upon the manner in which the present invention is programmed. Given the teachings herein, one of ordinary skill in the related art will be able to contemplate these and similar implementations or configurations of the present invention. Indeed, while the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

What is claimed is:

1. A method for augmented reality navigation during a medical intervention, said method comprising the steps of:
providing stereoscopic head mounted display, said display including a pair of stereo viewing cameras, at least one tracking camera, and a stereoscopic guidance display;
providing a plurality of markers on a frame attached to a table;
providing a medical instrument for performing said medical intervention, and providing a plurality of markers on the instrument;
during a medical intervention on a patient positioned on said table, determining a rigid body transformation between the tracking camera and the frame markers, and determining said patient's body pose from said rigid body transformation;
determining the pose of said medical instrument with respect to the table from the patient's body pose and said instrument markers;
displaying in the stereoscopic guidance display a visual representation of said patient, said instrument, and a path for guiding said instrument to perform said medical intervention, wherein the visual representation of said patient and said instrument is generated based on a signal received from said viewing cameras, and wherein the visual representation of said patient is overlaid with a medical image of a target of said intervention; and
color-coding the visual representation of the medical instrument to indicate penetration of said medical instrument toward said target in real-time to show the time evolution of the medical instrument's trajectory.

2. The method of claim 1, further comprising the step of, prior to the medical intervention, determining a rigid body transformation between the tracking camera and the viewing cameras.

3. The method of claim 1, further comprising the step of, prior to the medical intervention, determining a relationship between the medical image and the tracking camera.

4. The method of claim 3, further comprising providing a calibration phantom for determining a relationship between the medical image and the tracking camera, wherein said calibration phantom includes magnetic and optical markers.

5. The method of claim 1, further comprising monitoring the patient's respiration during said intervention, and altering said visual representation of said patient in accordance with said respiration.

6. The method of claim 1, wherein said image of said target is a magnetic resonance image.

7. The method of claim 1, wherein said instrument is a biopsy needle.

8. The method of claim 1, wherein the tracking camera is sensitive to the near-infrared spectrum, and comprises a wide angle lens and a ring shaped infrared flash.

9. The method of claim 1, further comprising a plurality of tracking cameras for positioning the head mounted display.

10. A program storage device readable by a computer, tangibly embodying a program of instructions executable by the computer to perform the method steps for augmented reality navigation during a medical intervention, said method comprising the steps of:
determining a rigid body transformation between a tracking camera and a plurality of frame markers attached to a table;
determining a patient's body pose from said rigid body transformation;
during a medical intervention on said patient, wherein said patient is positioned on said table, determining the pose of a medical instrument with respect to the table from the patient's body pose and a plurality of instrument markers;
providing a stereoscopic video-view of the patient in real-time in a stereoscopic head mounted display, said display including a pair of stereo viewing cameras, at least one tracking camera, and a stereoscopic guidance display;
displaying in the stereoscopic video-view a visual representation of said instrument, and a path for guiding said instrument to perform said medical intervention, wherein the visual representation of said patient is overlaid with an image of a target of said intervention; and
color-coding the visual representation of the medical instrument to indicate penetration of said medical instrument toward said target in real-time to show the time evolution of the medical instrument's trajectory.

11. The computer readable program storage device of claim 10, wherein the tracking camera is sensitive to the near-infrared spectrum, and comprises a wide angle lens and a ring shaped infrared flash.

12. The computer readable program storage device of claim 10, wherein the method further comprises the step of, prior to the medical intervention, determining a rigid body transformation between the tracking camera and a pair of stereo viewing cameras.

13. The computer readable program storage device of claim 10, wherein the method further comprises the step of, prior to the medical intervention, determining a relationship between the medical image and the tracking camera.

14. The computer readable program storage device of claim 13, wherein the method further comprises the step of providing a calibration phantom, said calibration phantom including magnetic and optical markers, wherein said calibration phantom is used to determine the relationship between the medical image and the tracking camera.

15. The computer readable program storage device of claim 10, wherein said method further comprises monitoring the patient's respiration during said intervention, and altering said visual representation of said patient in accordance with said respiration.

16. The computer readable program storage device of claim 10, wherein said image of said target is a magnetic resonance image.

17. The computer readable program storage device of claim 10, wherein said instrument is a biopsy needle.

18. A method for augmented reality navigation during a magnetic resonance guided intervention, said method comprising the steps of:
- providing stereoscopic head mounted display, said display including a pair of stereo viewing cameras, at least one tracking camera, and a stereoscopic guidance display;
- providing a biopsy needle for performing said intervention;
- providing a scanning table having a set of attached markers;
- providing a calibration phantom that includes magnetic and optical markers;
- determining a transformation between said at least one tracking camera and said scanning table by scanning said calibration phantom;
- during a medical intervention on a patient positioned on said table, determining said patient's body pose from a rigid body transformation between the tracking camera and the table;
- determining the pose of said biopsy needle with respect to the table from the patient's body pose;
- displaying in the stereoscopic guidance display a visual representation of said patient, said needle, and a path for guiding said needle to perform said intervention, wherein the visual representation of said patient and said needle is generated based on a signal received from said viewing cameras, and wherein the visual representation of said patient is overlaid with a magnetic resonance image of a target of said intervention; and
- displaying concentric circles in the guidance display to indicate distance of the needle to the target.

19. The method of claim 18, further comprising the step of, prior to said intervention, determining a rigid body transformation between the tracking camera and the viewing cameras.

20. The method of claim 18, wherein the tracking camera is sensitive to the near-infrared spectrum, and comprises a wide angle lens and a ring shaped infrared flash.

21. The method of claim 18, wherein said needle is provided with a plurality of markers, and wherein said markers are used in determining the pose of said needle.

22. The method of claim 18, further comprising providing a frame on said table, and providing a plurality of markers on said frame, wherein said markers are used to determine the rigid body transformation between said tracking camera and the patient's body.

* * * * *